United States Patent

Klauke et al.

[11] 4,093,669
[45] June 6, 1978

[54] METHOD FOR PREPARING TRICHLOROMETHYL-TRIFLUOROMETHYL-BENZENES

[75] Inventors: Erich Klauke, Odenthal; Gerhard Büttner, Cologne, both of Germany

[73] Assignee: Bayer Aktiengesellschaft, Leverkusen, Germany

[21] Appl. No.: 731,479

[22] Filed: Oct. 12, 1976

[30] Foreign Application Priority Data

Nov. 3, 1975 Germany .............................. 2548970

[51] Int. Cl.² .............................................. C07C 25/00
[52] U.S. Cl. .................................................. 260/651 F
[58] Field of Search ..................................... 260/651 F

[56] References Cited

U.S. PATENT DOCUMENTS

| 1,967,244 | 5/1934 | Holt et al. .................... 260/651 F |
| 2,174,512 | 10/1933 | Holt et al. .................... 260/651 F |
| 3,457,310 | 7/1969 | Fischback et al. ................ 260/578 |

FOREIGN PATENT DOCUMENTS

| 4,328,086 | 3/1968 | Japan ......................... 260/651 F |
| 1,416,181 | 12/1975 | United Kingdom ............ 260/651 F |

Primary Examiner—O. R. Vertiz
Assistant Examiner—Wayne A. Langel
Attorney, Agent, or Firm—Burgess, Dinklage & Sprung

[57] ABSTRACT

A process for the preparation of a trichloromethyl-trifluoromethyl-benzene of the formula

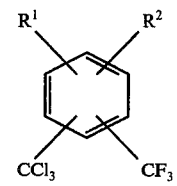

wherein
$R^1$ and $R^2$ are identical or different and represent hydrogen, fluorine or chlorine,
by contacting at least one molecule of the formula

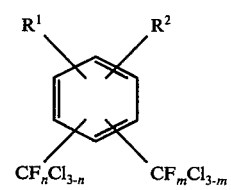

wherein
$R^1$ and $R^2$ are as previously identified, $m$ and $n$ are independently 0 to 3
with another molecule of the formula

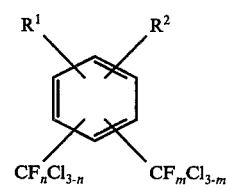

wherein
$m$ and $n$ are independently 0 to 3
in the presence of a halogen transfer catalyst, optionally in the presence of a promoter.

9 Claims, No Drawings

METHOD FOR PREPARING TRICHLOROMETHYL-TRIFLUOROMETHYL-BENZENES

The invention relates to a process for the preparation of trichloromethyl-trifluoromethyl-benzenes from partially fluorinated and chlorinated xylenes.

It is known to chlorinate the trifluoromethyl group in trifluoromethylbenzene with the aid of aluminium chloride and acetyl chloride (J. Amer.Chem.Soc. 60, 1697 (1938)). The chlorination of m- and p-bis-(trifluoromethyl)-benzenes with the aid of aluminium chloride is known from Z.obsc.chim. 37, 1626 (1967) and the chlorination of 3,5-bis-(trifluoromethyl)-nitrobenzene is known from U.S. Pat. No. 3,457,310. However, the reactions described here proceed with low yields, relative to the starting compounds, and with low selectivity.

SUMMARY OF THE INVENTION

Broadly, this invention contemplates a process for the preparation of a trichloromethyl-trifluoromethylbenzene of the formula

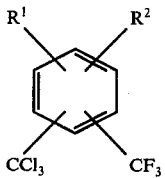

I wherein
$R^1$ and $R^2$ are identical or different and represent hydrogen, fluorine or chlorine,
which comprises contacting at least one molecule of the formula

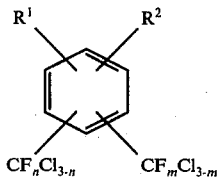

II with another molecule of the formula

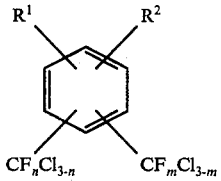

II wherein
$n$ and $m$ are independently 0 to 3
in the presence of a halogen transfer catalyst, optionally in the presence of a promoter. It should be understood that the present invention contemplates the reaction of one mol of a compound of the formula set forth at Formula II with another mol of the same formula. However, generally speaking, there is contemplated the reaction of one compound of the Formula II set forth supra with another compound falling within the same generic formula. The invention can be more readily understood when reference is made to the general discussion below, including the discussion of the reaction and the examples. The process takes place in the presence of a halogen transfer catalyst and preferably in the presence of a promoter.

From the above, it is evident that there is particularly contemplated the reaction of one xylene which has mixed fluorinated and chlorinated side chains with another xylene which has mixed fluorinated and chlorinated side chains.

A process for the preparation of trichloromethyl-trifluoromethyl-benzenes of the formula

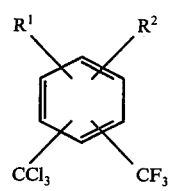

I wherein
$R^1$ and $R^2$ are identical or different and represent hydrogen, fluorine or chlorine,
has now been found, in which xylenes which have mixed fluorinated and chlorinated side chains and are of the formula

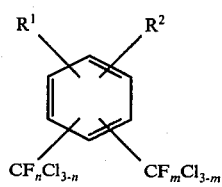

II wherein
$R^1$ and $R^2$ have the abovementioned meaning and $m$ and $n$ represent 0 to 3,
are treated with a halogen transfer catalyst, optionally in the presence of a promoter. tin.

The process according to the invention can be illustrated by the following reaction equation for the reaction of 1-difluoro-chloromethyl-3-trifluoromethyl-benzene with 1-dichloro-fluoromethyl-3-trichloro-methyl-benzene.

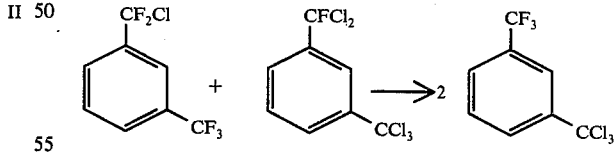

Xylenes of the formula II which have mixed fluorinated and chlorinated side chains can be employed as starting compounds for the process according to the invention. The relative ratio of the distribution of the chlorine and fluorine atoms to one another in the side chains is not significant for the process according to the invention.

It is possible to employ both the pure compounds and mixtures of these compounds. Thus, according to the process of the invention, it is possible, for example, to employ xylenes which contain five chlorine atoms and only one fluorine atom in the side chains or to employ mixtures of xylenes which have a different degree of chlorination and/or fluorination.

It is not necessary to employ stoichiometric amounts of the starting compounds for the process according to the invention. Crude fluorination mixtures which consist of xylenes perchlorinated in the side chains and which are obtained when 1 mol of bis-(trichloromethyl)-benzene is reacted with less than 6 mols of anhydrous hydrogen fluoride can be employed preferentially in the process according to the invention.

The xylenes having mixed fluorinated and chlorinated side chains can, for example, be reacted according to processes, which are in themselves known, for non-catalytic fluorination of bis-(trichloromethyl)-benzenes (Houben-Weyl, Volume V/3, page 121-123) with less than the six-fold amount of hydrogen fluoride. The following starting compounds may be mentioned as examples: 1-fluorodichloromethyl-3-trichloromethyl-benzene, 1-fluorodichloromethyl-4-trichloromethyl-benzene, 1,3-bis-(fluorodichloromethyl)-benzene, 1,4-bis-(fluorodichloromethyl)-benzene, 2,4-bis-(fluorodichloromethyl)-chlorobenzene, 2,6-bis-(fluorodichloromethyl)-chlorobenzene, 2,5-bis-(fluorodichloromethyl)-chlorobenzene, 2,6-bis-(fluorodichloromethyl)-fluorobenzene, 2,4-bis-(fluorodichloromethyl)-fluorobenzene, 2,5-bis-(fluorodichloromethyl)-1,4-dichlorobenzne, 1-fluorodichloromethyl-3-difluorochloromethylbenzene, 1-fluorodichloromethyl-4-difluorochloromethyl-benzene, 1,3-bis-(difluorochloromethyl)-benzene, 1,4-bis-(difluorochloromethyl)-benzene, 1,3-bis-(difluorochloromethyl)-5-chlorobenzene, 1,3-bis-(difluorochloromethyl)-5-bromobenzene, 1,4-bis-(difluorochloromethyl)-2-fluorobenzene, 1,4-bis-(difluorochloromethyl)-2-chlorobenzene, 1,3-bis-(difluorochloromethyl)-2-chlorobenzene, 1,4-bis-(difluorochloromethyl)-2,5-dichlorobenzene, 3-difluorochloromethyl-benzotrifluoride, 4-difluorochloromethyl-benzotrifluoride, 2-chloro-3-difluorochloromethyl-benzotrifluoride, 4-chloro-3-difluorochloromethylbenzotrifluoride, 4-bromo-3-difluorochloromethyl-benzotrifluoride and 2-fluoro-3-difluorochloromethyl-benzotrifluoride.

Halogen transfer catalysts, such as can be employed for the process according to the invention, are in themselves known (Houben-Weyl, Volume V/3, 125 (1962)). Examples which may be mentioned are iron trichloride, titanium tetrachloride, aluminium chloride and antimony-V halides, such as antimony pentachloride, antimony pentafluoride and antimony-V chloride-fluoride, preferably antimony pentachloride.

In general, the halogen transfer catalysts are employed, for the process according to the invention, in amounts of 0.1 to 5% by weight and preferably of 1 to 3% by weight. Antimony pentachloride is preferably used in amounts of 0.1 to 1% by weight and particularly preferentially of 0.25 to 0.75% by weight. It can be appropriate to add the total amount in 2 or more portions.

For the process according to the invention it can be advantageous to work in the presence of promoters. Promoters which may be mentioned are those compounds which form a complex anion with the catalyst. Examples of promoters which may be mentioned are metal chlorides, such as sodium chloride and potassium chloride, and hydrogen chloride, preferably hydrogen chloride.

In general, the process according to the invention is carried out at temperatures of about 0° to 170° C, preferably of 20° to 120° C and particularly preferentially of 40° to 80° C.

In general, the process according to the invention is carried out without using a solvent. However, in certain circumstances it can be advantageous to carry out the reaction in the presence of a solvent or diluent; in this case all the solvents or diluents which are also suitable for carrying out Friedel-Crafts reactions can be employed. Preferred examples which may be mentioned are carbon disulphide and nitrobenzene.

If a promoter is employed, the catalyst and the promoter are advantageously employed in a molar ratio of 1 to 0.1 up to 1 and preferably in equivalent amounts.

It is also possible to pass the promoter, for example hydrogen chloride, continuously through the reaction mixture during the reaction or to carry out the reaction under excess pressure of the promoter.

The process according to the invention can be carried out under reduced pressure, normal pressure or excess pressure; however, in general it is appropriate to carry out the reaction under normal pressure or excess pressure. The use of excess pressure is subject only to limits imposed by the apparatus. Appropriately, the reaction is carried out in the pressure range between 1 and 50 bars and preferably 10 to 30 bars.

The optimum amount of the catalyst and of the promoter and the suitable reaction temperature are dependent on the starting material and the nature of the catalyst.

The process according to the invention can be carried out as follows:

The partially fluorinated and chlorinated xylene and the catalyst, optionally in a solvent or diluent, are initially introduced into a reaction vessel, optionally into an autoclave. If a promoter is to be used, this is also added at the start of the reaction. The reaction mixture is brought to the chosen reaction temperature and the chosen reaction pressure whilst stirring.

When the reaction has ended, the catalyst is either filtered off or hydrolysed with water in the presence of an acid and then filtered off. However, it is optionally also possible to separate off the catalyst, for example antimony pentachloride, by fractional vacuum distillation and to recycle it into the process according to the invention.

Optionally, the catalyst can also be bound by means of an absorbent, for example active charcoal, silica gel, fuller's earth or zeolites, and then separated off by filtration.

The trifluoromethyl-trichloromethyl-benzene formed can, for example, be isolated by fractional distillation and then purified.

A particular advantage of the process according to the invention is that the first runnings and last runnings obtained from the fractional distillation for isolation of the trichloromethyl-trifluoromethyl-benzene can be re-employed in a new reaction according to the process of the invention. A virtually quantitative conversion of the xylenes employed, which have mixed fluorinated and chlorinated constituents, is achieved by this procedure.

It is surprising that trichloromethyl-trifluoromethyl-benzenes can be prepared selectively and in high yields from xylenes which have mixed chlorinated and fluorinated side chains.

The process according to the invention makes it possible, in a particularly advantageous manner, to employ mixtures of different partially chlorinated and fluorinated xylenes. Mixtures which are necessarily obtained as a by-product from another reaction, for example the chlorination of bis-(trifluoromethyl)-benzenes, can also be employed. With the aid of the process according to the invention it is possible to convert the by-products which are necessarily obtained into trichloromethyl-trifluoromethyl-benzenes. The trichloromethyl-trifluoromethyl-benzenes can be reacted with benzene in the presence of aluminum chloride in a Friedel-Crafts-reaction to fungicides (DOS (German Published Specification No. 1,795,249)). Moreover they are intermediates for dyestuffs (DOS (German Published Specification No. 2,364,475)).

The trichloromethyl-trifluoromethyl-benzenes themselves have a bactericidal and fungicidal action (U.S. Pat. No. 3,457,310).

EXAMPLE 1

70 g of 1,3-bis-(fluorodichloromethyl)-benzene are initially introduced into a glass flask and 0.7 g of antimony pentachloride is added. On the addition of the catalyst, the reaction mixture warms up to 42° C. The reaction mixture is heated further up to 80° C and kept at this temperature for 1 hour. After cooling, the mixture is washed once with dilute hydrochloric acid and then with water. The organic phase is separated off and dried.

Analysis of the reaction product by gas chromatography gives the following composition: 36.6% of 1,3-bis-(trichloromethyl)-benzene, 4.1% of 1-(dichlorofluoromethyl)-3-(trichloromethyl)-benzene, 6.1% of 1-(chloro-difluoromethyl)-3-(trichloromethyl)-benzene, 44.9% of 1-(trifluoromethyl)-3-(trichloromethyl)-benzene, 2.5% of 1-(trifluoromethyl)-3-(dichloro-fluoromethyl)-benzene, 2.9% of 1-(trifluoromethyl)-3-(chlorodifluoromethyl)-benzene and 2.4% of 1,3-bis-(trifluoromethyl)-benzene.

28 g of 1-(trifluoromethyl)-3-(trichloromethyl)-benzene (boiling point$_{11}$: 87° C; $n_{20}^D$: 1.4885) are obtained by distillation; this corresponds to a yield of 63.5%,

EXAMPLE 2

200 g of 1,3-bis-(difluorochloromethyl)-benzene and 2 g of antimony pentachloride are initially introduced into an autoclave and the mixture is stirred at 60° C for 45 minutes under a hydrogen chloride pressure of 20 bars.

When the reaction has ended, the mixture is allowed to cool and the pressure is let down. The catalyst is hydrolysed by adding water and separated off by filtration. The reaction mixture is washed once with dilute hydrochloric acid and then with water. The organic phase is separated off and dried.

Analysis of the reaction product by gas chromatography gives the following composition: 4.1% of 1,3-bis-(trichloromethyl)-benzenes, 0.8% of 1-(dichlorofluoromethyl)-3-(trichloromethyl)-benzene, 1.9% of 1-(chloro-difluormethyl)-3-(trichloromethyl)-benzene, 52.0% of 1-(trifluoromethyl)-3-(trichloromethyl)-benzene, 5.1% of 1-(trifluoromethyl)-3-(dichloro-fluoromethyl)-benzene, 9.2% of 1-(trifluoromethyl)3-(chlorodifluoromethyl)-benzene and 26.2% of 1,3-bis-(trifluoromethyl)-benzene.

Fractional distillation of the reaction product gives, under 11 mm Hg and at 87° C, 92 g of 1-(trifluoromethyl)-3-(trichloromethyl)-benzene; this corresponds to a yield of 64.7%.

Preparation of the high fluorinated starting material

3 Kg of 1,3-bis-(trichloromethyl-benzene are fluorinated with 2 l of anhydrous hydrogen fluoride at 50° C for 6 hours in an autoclave.

When the reaction has ended, the mixture is cooled and the pressure is let down; the reaction mixture is poured onto ice and the organic phase is separated off and washed twice with water. The reaction mixture is subjected to fractional distillation; 1-trifluoromethyl-3-difluorochloromethyl-benzene (boiling point: 146° C, $n_{20}^D$: 1.4182) and and 1-difluorochloromethyl-3-fluorodichloromethyl-benzene (boiling point: 179° C, $n_{20}^D$: 1.4562) are isolated.

Preparation of the low fluorinated starting material 4 kg of 1,3-bis-(trichloromethyl)-benzene are fluorinated with 639 g of anhydrous fluoride at 100° C for 2½ hours in an autoclave. When the reaction has ended, the mixture is cooled and the pressure is let down; the reaction mixture is poured onto ice and the organic phase is separated off and washed with water.

Analysis of the reaction mixture by gas chromatography gives the following composition: 0.9% of 1,3-bis-(trichloromethyl)-benzene, 12.6% of 1-trichloromethyl-3-fluorodichloromethyl-benzene, 50.3% of 1,3-bis-(fluorodichloromethyl)-benzene, 20.5% of 1-difluorochloromethyl-3-fluorodichloromethyl-benzene and 10.2 of 1,3-bis-(difluorochloromethyl)-benzene.

EXAMPLE 3

45 g of 1-trichloromethyl-3-fluorodichloromethylbenzene and 35 g of 1-trifluoromethyl-3-difluorochloromethylbenzene are initially introduced into a glass flask and 0.8 g of antimony pentachloride is added. After a slightly exothermic reaction has subsided, the reaction mixture is stirred for 1½ hours at 60° C.

When the reaction has ended, the mixture is washed once with dilute hydrochloric acid and then with water.

Analysis of this reaction mixture by gas chromatography indicates the following composition: 13.9% of 1,3-bis(trichloromethyl)-benzene, 3.3% of 1-(dichlorofluoromethyl)-3-(trichloromethyl)-benzene, 8.7% of 1-(chloro-difluoromethyl)-3-(trichloromethyl)-benzene, 47.6% of 1-(trifluoromethyl)-3-(trichloromethyl)-benzene, 6.7% of 1-(trifluoromethyl)-3-(dichloro-fluoromethyl)-benzene, 12.7% of 1-(trifluoromethyl)-3-(chloro-difluoromethyl)-benzene and 2.4% of 1,3-bis-(trifluoromethyl)-benzene.

1-(Trifluoromethyl)-3-(trifluoromethyl)-benzenes (boiling point$_{11}$ : 87° Cl $n_{20}^D$ : 1.4885) are obtained by distillation.

EXAMPLE 4

200 g of the mixture of fluorinated and chlorinated xylenes obtained under A) are reacted with 0.5 g of antimony pentachloride at 40° C for 5 hours.

When the reaction has ended, the mixture is cooled and washed once with dilute hydrochloric acid or with water. The organic phase is separated off and dried.

Analysis of the reaction product by gas chromatography gives the following composition: 26.9% of 1,3-bis-(trichloromethyl)-benzene, 6.9% 1-(dichlorofluoromethyl)-3(trichloromethyl)-benzene, 17.0% of 1-(chlorodifluoromethyl)-3-(trichloromethyl)-benzene, 30.1% of 1-(trifluoromethyl)-3-(trichloromethyl)-benzene, 6.0% of 1-(trifluoromethyl)-3-(dichlorofluoromethyl)-benzene, 7.7% of 1-(trifluoromethyl)-3-(chlorodifluoromethyl)-benzene and 1.0% of 1,3-bis-(trifluoromethyl)benzene.

Preparation of the starting material for Examples 5 to 7:

1,250 g of 4-trichloromethyl-benzotrichloride and 240 g of hydrogen fluoride are initially introduced into a 2 l autoclave which has a reflux condenser, cooled to −10° C, and a pressure regulating valve. Nitrogen is passed into the autoclave and the mixture is then heated to 100° C under a nitrogen pressure of 2 bars. During the reaction the pressure rises to 25 bars; whilst maintaining this pressure, the hydrogen chloride formed is released continuously.

The reaction has ended after about 2 hours. According to gas chromatography, the reaction product has the following composition:

| Number of fluorine atoms in the side chain of the xylene formed proportion determined by analysis by gas chromatography | 0 | 1 | 2 | 3 | 4 | 5 | 6 |
|---|---|---|---|---|---|---|---|
| | — | 6.59% | 36.57% | 33.69% | 19.735 | 1.59% | — |

The following compounds are obtained by fractional distillation : 1-(fluoro-dichloromethyl)-4-(trichloromethyl)benzene (boiling point$_{12}$: 144° C, melting point: 52°–54° C), 1-fluoro-dichloromethyl)- 4-(fluoro-dichloromethyl)-benzene (boiling point$_{12}$: 119° C; melting point: 37°–39° C), 1-(difluorochloromethyl)-4-(fluoro-dichloromethyl)-benzene (boiling point$_{12}$: 92° C; $n_D^{20}$: 1.4883), 1-difluoro-chloromethyl)-4-(difluoro-chloromethyl)-benzene (boiling point: 179°–180° C; $n_D^{20}$ : 1.4537) and 1-(trifluoromethyl)-4-(difluoro-chloromethyl)-benzene (boiling point: 148° C; $n_D^{20}$: 1.4168).

EXAMPLE 5

50 g of 1,4-bis-(difluorochloromethyl)-benzene and 1 g of aluminium chloride are initially introduced into a 0.5 l autoclave, hydrogen chloride is introduced up to a pressure of 2 bars and the mixture is then heated up to 140° C. The mixture is stirred for 2 hours at 140° C and cooled, the pressure is let down and the mixture is filtered. The filtrate has the following composition, determined by gas chromatography:

| halogen atoms per molecule | 6 Cl | 1 F 5 Cl | 2 F 4 Cl | 3 F 3 Cl | 4 F 2 Cl | 5 F 1 Cl | 6 F |
|---|---|---|---|---|---|---|---|
| gas chromatography: | 2.8 | 2.1 | 3.9 | 37.6 | 6.7 | 8.1 | 38.7 |

17 g (which correspond to a yield of 47.8%) of 4trichloromethyl-benzotrifluoride, which has a boiling point$_{12}$:of 90° C and a $n_D^{20}$ of 1.4891, are obtained from the filtrate by fractional distillation.

EXAMPLE 6

56 g of 1,4-bis-(fluorodichloromethyl)-benzene and 21 g of 1,4-bis-(trifluoromethyl)-benzene together with 0.8 g of antimony pentachloride are initially introduced into an autoclave and the mixture is stirred for 2 hours at 140° C under a hydrogen chloride pressure of 28 bars.

After cooling and letting down, the reaction mixture is washed one with dilute hydrochloric acid and and once with water. According to analysis by gas chromatography, the crude product contains 36.4% of 4-trichloromethyl-benzotrifluoride and this is isolated, by distillation, in a yield of 25 g (which corresponds to a yield of 31.5% as a liquid which has a boiling point$_{14}$ of 93°–94° C.

EXAMPLE 7

56 g of 1,4-bis-(fluorodichloromethyl)-benzene and 21 g of 1,4-bis-(trifluoromethyl)-benzene and 0.8 g of antimony pentafluoride are initially introduced into an autoclave and the mixture is stirred for 1 hour at 140° C under a hydrogen chloride pressure of 29 bars.

After cooling and letting down, the reaction mixture is washed once with dilute hydrochloric acid and once with water. According to analysis by gas chromatography, the crude product contains 35.2% of 4-trichloromethyl-benzotrifluoride and this is isolated by distillation, in a yield of 24 g (which corresponds to yield of 30.3%), as a liquid which has a boiling point of boiling point$_{14}$: 93°–94° C.

Preparation of the starting material for Examples 8 to 10:

1,043 of of 2,5-bis-(trichloromethyl)-chlorobenzene and 180 g of anhydrous hydrogen fluoride are initially introduced into a 2 l autoclave. The reaction mixture is heated to 100° C, whilst stirring, for about 2 hours until the evolution of hydrogen chloride has ceased. During the reaction, the pressure in the autoclave rises up to 25 bars; whilst maintaining this pressure, hydrogen chloride is released continuously.

When the reaction has ended, the reaction mixture is cooled and the pressure is let down.

Analysis by gas chromatography gives the following composition:

| number of fluorine atoms in the side chain of the xylene formed proportion determined by analysis by gas chromatography | 0 | 1 | 2 | 3 | 4 | 5 | 6 |
|---|---|---|---|---|---|---|---|
| | — | 5.6 | 48.4 | 32.8 | 5.5 | 0.5 | — |

The proportion of more highly fluorinated xylenes can be increased by employing 4 mols of hydrogen fluoride per mol of the starting compound.

The following compounds are obtained by fractional distillation: 2,5-bis-(fluoro-dichloromethyl)-chlorobenzene (boiling point$_{13}$: 142° C; $n_D^{20}$: 1.5440) and 2,5-bis-(difluoro-chloromethyl)-chlorobenzene (boiling point$_{13}$: 92°–93° C; $n_D^{20}$: 1.4810).

EXAMPLE 8

50 g of 2,5-bis-(dichlorofluoromethyl)-chlorobenzene and 0.5 g of antimony pentachloride are stirred, in an autoclave, for 3 hours at 80° C and under a hydrogen chloride pressure of 25 bars.

When the reaction has ended, the pressure is let down and the mixture is washed with dilute hydrochloric acid and with water and then subjected to fractional distillation. 20 g (which correspond to a yield of 63.5%) of 2-trichloromethyl-5-trifluoromethyl-chlorobenzene (boiling point$_{12}$: 113°–114 C; $n_D^{20}$: 1.5111) are obtained.

EXAMPLE 9

50 g of 2,5-bis-(difluorochloromethyl)-chlorobenzene and 0.5 g of antimony pentachloride are stirred, in an autoclave, for 3 hours at 80° C and under a hydrogen chloride pressure of 25 bars.

When the reaction has ended, the pressure is let down

| number of halogen atoms in the side chains of the xylene formed | 6 Cl 0 F | 5 Cl 1 F | 4 Cl 2 F | 3 Cl 3 F | 2 Cl 4 F | 1 Cl 5 F | 0 Cl 6 F |
|---|---|---|---|---|---|---|---|
| proportion determined by analysis by gas chromatography | 5.1% | 2.9% | 6.2% | 35.4% | 10.1% | 16.1% | 22.3% | and the mixture is washed with dilute hydrochloric acid and with water and then subjected to fractional distillation. 18,5 g (which correspond to a yield of 58.7%) of 2-trichloromethyl-5-trifluoromethyl-chlorobenzene are obtained.

EXAMPLE 10

56.6 g of 2,5-bis-(difluorochloromethyl)-chlorobenzene and 63 g of 2,5-1,5-bis-(fluorodichloromethyl)-chlorobenzene are reacted with 1.7 g of antimony pentachloride for 2 hours in an autoclave at 90° C and under a hydrogen chloride pressure of 25 atmospheres gauge.

When the reaction has ended, the mixture is cooled and the pressure is let down; the reaction mixture is then stirred twice with, in each case, 2 g of finely powdered and freshly dried active charcoal and then filtered.

The reaction product has the following composition, determined by gas chromatography:

| number of halogen atoms in the side chains of the xylene formed | 6 Cl 0 F | 5 Cl 1 F | 4 Cl 2 F | 3 Cl 3 F | 2 Cl 4 F | 1 Cl 5 F | 0 Cl 6 F |
|---|---|---|---|---|---|---|---|
| proportion determined by analysis by gas chromatography | 5.7% | 3.6% | 11.9% | 57.9% | 7.6% | 10.9% | 0.9% |

65 g of trichloromethyl-trifluoromethyl-chlorobenzene are obtained by fractional distillation.

Preparation of the starting material for Examples 11 and 12.

2,4-Bis-(fluorodichloromethyl)-chlorobenzene (boiling point$_{14}$: 139°–142° C; $n_D^{20}$: 1.5442) and 2,4-bis-(difluorochloromethyl)-chlorobenzene (boiling point$_{14}$: 93°–95° C; $n_D^{20}$: 1.4840) are obtained by fluorinating 2,4-bis-(trichloromethyl)-chlorobenzene with hydrogen fluoride under the same conditions as those described for the preparation of the starting material for Examples 8–10.

EXAMPLE 11

35 g of 2,4-bis-(difluoro-chloromethyl)-chlorobenzene and 0.35 g of antimony pentachloride are stirred, in an autoclave, for 2 hours at 110° C under a hydrogen chloride pressure of 20 bars.

When the reaction has ended, the mixture is cooled, the pressure is let down and the mixture is then washed with dilute hydrochloric acid and water.

The reaction product has the following composition, determined by gas chromatography:

11.5 g of 2-trifluoromethyl-4-trichloromethyl-chlorobenzene (boiling point$_{12}$: 117° C; $n_D^{20}$: 1.5158) are obtained by fractional distillation.

Example 12

35 g of 2,4-bis-(fluoro-dichloromethyl)-chlorobenzene are reacted under the same reaction conditions as in Example 11.

The reaction product has the following composition: determined by gas chromatography:

| number of halogen atoms in the side chains of the xylene formed | 6 Cl 0 F | 5 Cl 1 F | 4 Cl 2 F | 3 Cl 3 F | 2 Cl 4 F | 1 Cl 5 F | 0 Cl 6 F |
|---|---|---|---|---|---|---|---|
| proportion determined by analysis by gas chromatography | 33.1% | 10.6% | 10.9% | 35.5% | 3.9% | 3.1% | 2.8% |

Preparation of the starting material for Examples 13 to 15.

620 g of 2,6-bis-(trichloromethyl)-chlorobenzene and 126 g of anhydrous hydrogen fluoride are initially introduced into an autoclave and the mixture is heated to 100° C for 1 hour, whilst stirring.

When the reaction has ended, the mixture is cooled and the pressure is let down; the mixture is then washed with water and dried.

The following compounds are obtained by fractional distillation: 2-(trifluoromethyl)-6-(difluoro-chloromethyl)chlorobenzene (boiling point: 192°–194° C; $n_D^{20}$: 1.4549), 2-(difluoro-chloromethyl)-6-(difluoro-chloromethyl)-chlorobenzene (boiling point$_{14}$: 102°–104° C; $n_D^{20}$: 1.4071), 2-(difluorochloromethyl)-6-(fluoro-dichloromethyl)-chlorobenzene (boiling point$_{13}$: 123°–125° C; $n_D^{20}$: 1.5198) and 2-(fluoro-dichloromethyl)-6-(fluoro-dichloromethyl)-chlorobenzene (boiling point$_{13}$: 148°–150° C; $n_D^{20}$: 1.5507).

EXAMPLE 13

45 g of 2,6-bis-(fluoro-dichloromethyl)-chlorobenzene are reacted with 0.45 g of antimony pentachloride, in a stirred autoclave, in the course of 30 minutes at 120° C and under a hydrogen chloride pressure of 20 bars.

When the reaction has ended, the mixture is cooled and the pressure is let down; the reaction product is washed with dilute hydrochloric acid and then with water and dried.

Analysis by gas chromatography gives a proportion of 41.4% of 2-trifluoromethyl-6-trichloromethyl-chlorobenzene.

After a fractional distillation, 17 g (which correspond to a yield of 59.5%) of 2-trifluoromethyl-6-trichloromethyl-chlorobenzene are obtained at a boiling point$_{14}$ of 129°–131° C. Melting point: 32°–33° C.

EXAMPLE 14

45 g of 2,6-bis-(difluoro-chloromethyl)-chlorobenzene are reacted with 0.45 g of antimony pentachloride, in a stirred autoclave, in the course of 30 minutes at 120° C and under a hydrogen chloride pressure of 20 bars.

When the reaction has ended, the mixture is cooled and the pressure is let down; the reaction product is washed with dilute hydrochloric acid and then with water and dried.

Analysis by gas chromatography gives a proportion of 37.4% of 2-trifluoromethyl-6-trichloromethyl-chlorobenzene.

EXAMPLE 15

2 g of sodium tetrachloroaluminate (prepared by mixing molar amounts of sodium chloride and aluminium chloride) are added to 50 g of 2-(difluorochloromethyl)-6-(fluoro-dichloromethyl)-chlorobenzene and the mixture is stirred for 1 hour at 150° C.

When the reaction has ended, the inorganic constituent of the reaction mixture is filtered off.

Analysis by gas chromatography gives a proportion of 34.9% of 2-trifluoromethyl-6-trichloromethyl-chlorobenzene.

Preparation of the starting material for Examples 16 and 17 a. Preparation of 1,3-difluoro-4,6-bis-(trichloromethyl)benzene 1.8 l of anhydrous hydrogen fluoride are initially introduced into a stirred vessel made of stainless steel and 625 g of 1,3-dimethyl-4-fluoro-aniline (see Am. Soc. 54, 2981) are introduced, whilst cooling. A diazotisation reaction is then carried ut at 0° C by adding 374 g of sodium nitrite in portions. The mixture is then heated slowly to room temperature. Since splitting of the diazonium fluoride proceeds only slowly at this temperature, the temperature is raised up to the reflux temperature of the solution. Towards the end of the reaction 800 ml of dimethylsulphoxide are added and the temperature is further raised up to 80° C and this temperature is maintained for 30 minutes. The reaction mixture is then poured onto ice, the mixture is extracted with methylene chloride and the organic phase is separated off, dried over sodium sulphate and then distilled. 428 g of 1,3-difluoro-4,6-dimethylbenzene, which has a boiling point of 143° C and a melting point of 30° to 31° C, are obtained.

735 g of the 1,3-difluoro-4,6-dimethylbenzene prepared as described above are treated with chlorine gas, whilst irradiating with UV light and slowly warming in the temperature range from 110° to 190° C, until no further chlorine is taken up.

1,516 g of 1,3-difluoro-4,6-bis-(trichloromethyl) benzene, which has a boiling point of 156° C/12 mm Hg and a melting point of 77° to 79° C, are obtained by distilling the reaction product under reduced pressure.

b. Preparation of 4,6-difluoro-1,3-bis-(fluorodichloromethyl)benzene 525 g of 4,6-difluoro-1,3-bis-(trichloromethyl)benzene and 90 g of anhydrous hydrogen fluoride are initially introduced into an autoclave. The autoclave is closed, nitrogen is introduced, as the blanketing gas, under a pressure of 2 bars and the mixture is slowly heated up to 80° C. When this temperature has been reached, the stirrer is switched on and the hydrogen chloride liberated during the fluorination is released continuously via a valve, whilst maintaining a pressure of 24 bars. After 2.5 hours at a reaction temperature of 80° to 100° C, the chlorine/fluorine exchange has ended. The mixture is cooled, the pressure is let down and the liquid reaction mixture is washed with dilute aqueous hydrochloric acid and then with water.

455 g of a crude product ($n_D^{20}$: 1.4893) are obtained and 220 g of 4,6-difluoro-1,3-bis-(fluorodichloromethyl)benzene, which has a boiling point of 108° to 109° C/11 mm Hg and a $n_D^{20}$ of 1.5008, are obtained from this by fractional distillation.

EXAMPLE 16

50 g of 4,6-difluoro-1,3-bis-(fluorodichloromethyl)-benzene are initially introduced into a glass flask and 0.5 g of antimony pentachloride is added at 70° C. On addition of the catalyst, the reaction mixture warms to about 90° C. The reaction mixture is kept at this temperature for two hours, whilst at the same time passing hydrogen chloride through the mixture. The reaction mixture is then cooled and washed once with dilute hydrochloric acid and then with water. Analysis of the dried organic phase by gas chromatography gives the following composition for the crude product of the formula

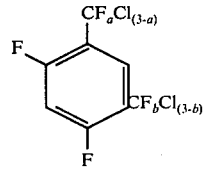

| number of fluorine atoms in the side chain of the xylene | 0 | 1 | 2 | 3 | 4 | 5 | 6 |
|---|---|---|---|---|---|---|---|
| proportion determined by analysis by gas chromatography | 35.6 | 10.0 | 13.3 | 30.3 | 4.7 | 4.6 | 0.5 |

The following fractions are obtained by fractional distillation:

| Fraction I | boiling range 27 to 83° C / 11 mm Hg | 5 g |
|---|---|---|
| Fraction II | boiling range 84 to 86° C / 11 mm Hg, $n_D^{20}$: 1.4712 | 13 g |
| Residue | | 26 g |

According to analysis by gas chromatography and the $19^F$ nuclear magnetic resonance spectrum, fraction II consists to the extent of 95% of 4,6-difluoro-1-trifluoromethyl-3-trichloromethylbenzene.

EXAMPLE 17

50 g of 4,6-difluoro-1,3-bis-(fluorodichloromethyl)-benzene are initially introduced into a glass flask and 0.5 g of antimony pentafluoride is added at 70° C. On addition of the catalyst, the reaction mixture warms to about 90° C. The reaction mixture is kept at this temperature for four hours, whilst at the same time passing hydrogen chloride through the mixture. The reaction mixture is then cooled and washed once with dilute hydrochloric acid and then with water. Analysis of the dried organic phase by gas chromatography gives the following composition for the crude product of the formula indicated in Example 16.

| number of fluorine atoms in the side chain of the xylene | 0 | 1 | 2 | 3 | 4 | 5 | 6 |
|---|---|---|---|---|---|---|---|
| proportion determined by analysis by gas chromatography | 37.1 | 6.6 | 7.9 | 38.3 | 4.3 | 3.5 | 0.4 |

17 g of 4,6-difluoro-1-trifluorometyl-3-trichloromethylbenzene are obtained, as a liquid with a boiling range of 35° to 36° C/11 mm Hg, from the crude product by fractional distillation.

What is claimed is:

1. A process for the preparation of a trichloromethyl-trifluoromethyl-benzene of the formula

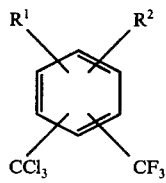

wherein
R¹ and R² are identical or different and represent hydrogen, fluorine or chlorine,
which comprises contacting at least one compound of the formula

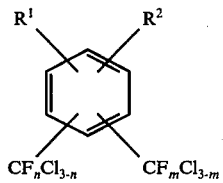

selected from the group consisting of 1-fluorodichloromethyl-3-trichloromethyl-benzene, 1-fluorodichloromethyl-4-trichloromethyl-benzene, 1,3-bis-(fluorodichloromethyl)-benzene, 1,4-bis-(fluorodichloromethyl)-benzene, 2,4-bis-(fluorodichloromethyl)-chlorobenzene, 2,6-bis-(fluorodichloromethyl)-chlorobenzene, 2,5-bis-(fluorodichloromethyl)-chlorobenzene, 2,6-bis-(fluorodichloromethyl)-fluorobenzene, 2,4-bis-(fluorodichloromethyl-fluorobenzene, 2,5-bis-(fluorodichloromethyl)-1,4-dichlorobenzene, 1-fluorodichloromethyl-3-difluorochloromethylbenzene, 1-fluorodichloromethyl-4-difluorochloromethyl-benzene, 1,3-bis-(difluorochloromethyl)-benzene, 1,4-bis-(difluorochloromethyl)-benzene, 1,3-bis-(difluorochloromethyl)-5-chlorobenzene, 1,3-bis-(difluorochloromethyl)-5-bromobenzene, 1,4-bis-(difluorochloromethyl)-2-fluorobenzene, 1,4-bis-(difluorochloromethyl)-2-chlorobenzene, 1,3-bis-(difluorochloromethyl)-2-chlorobenzene, 1,4-bis-(difluorochloromethyl)-2-chlorobenzene, 1,4-bis-(difluorochloromethyl)-2,5-dichlorobenzene, 3-difluorochloromethyl-benzotrifluoride, 4-difluorochloromethyl-benzotrifluoride, 2-chloro-3-difluorochloromethyl-benzotrifluoride, 4-chloro-3-difluorochloromethylbenzotrifluoride, 4-bromo-3-difluorochloromethyl-benzotrifluoride and 2-fluoro-3-difluorochloromethyl-benzotrifluoride with a compound of the formula

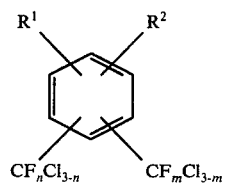

wherein
R¹ and R² have the previously assigned significance, said other compound also being selected from the group consisting of 1-fluorodichloromethyl-3-trichloromethyl-benzene, 1-fluorodichloromethyl-4-trichloromethyl-benzene, 1,3-bis-(fluorodichloromethyl)-benzene, 1,4-bis-(fluorodichloromethyl)-benzene, 2,4-bis-(fluorodichloromethyl)-chlorobenzene, 2,6-bis-(fluorodichloromethyl)-chlorobenzene, 2,5-bis-(fluorodichloromethyl)-chlorobenzene, 2,6-bis-(fluorodichloromethyl)-fluorobenzene 2,4-bis-(fluorodichloromethyl)-fluorobenzene, 2,5-bis-(fluorodichloromethyl)-1,4-dichlorobenzene, 1-fluorodichloromethyl-3-difluorochloromethylbenzene, 1-fluorodichloromethyl-4-difluorochloromethyl-benzene, 1,3-bis-(difluorochloromethyl)-benzene 1,4-bis-(difluorochloromethyl)-benzene, 1,3-bis-(difluorochloromethyl)-5-chlorobenzene, 1,3-bis-(difluorochloromethyl)-5-bromobenzene, 1,4-bis-(difluorochloromethyl)-2-fluorobenzene, 1,4-bis-(difluorochloromethyl)-2-chlorobenzene, 1,3-bis-(difluorochloromethyl)-2-chlorobenzene, 1,4-bis-(difluorochloromethyl)-2-chlorobenzene, 1,4-bis-(difluorochloromethyl)-2,5-dichlorobenzene, 3-difluorochloromethyl-benzotrifluoride, 4-difluorochloromethyl-benzotrifluoride, 2-chloro-3-difluorochloromethyl-benzotrifluoride, 4-chloro-3-difluorochloromethylbenzotrifluoride, 4-bromo-3-difluorochloromethyl-benzotrifluoride and 2-fluoro-3-difluorochloromethyl-benzotrifluoride in the presence of a halogen transfer catalyst.

2. A process according to claim 1 wherein the reaction is carried out in the presence of a promoter.

3. A process according to claim 2 wherein said promoter is hydrogen chloride.

4. A process according to claim 1 wherein the process is carried out at a temperature of 40° to 80° C.

5. A process according to claim 4 wherein the halogen transfer catalyst is selected from the group consisting of iron trichloride, titanium tetrachloride, aluminum chloride and an antimony V halide 6. A process according to claim 1 wherein the reaction is carried out employing antimony pentachloride as the halogen transfer catalyst.

7. A process according to claim 1 wherein a mixture of different xylenes having mixed fluorinated and chlorinated constituents are employed as reactants.

8. A process according to claim 1 wherein the reaction is carried out at a temperature of 0° to 170° c.

9. A process according to claim 1 wherein the process is carried out at a temperature of 20° to 170° C.

* * * * *

UNITED STATES PATENT AND TRADEMARK OFFICE
CERTIFICATE OF CORRECTION

PATENT NO. : 4,093,669
DATED : June 6, 1978
INVENTOR(S) : Erich Klauke et al

It is certified that error appears in the above-identified patent and that said Letters Patent are hereby corrected as shown below:

```
Column 2, line 43, after "promoter" delete "tin.".
Column 7, line 58, "4tri-" should read -- 4-tri- --.
Column 8, line 2, "one" should read -- once --.
Column 12, line 7, "(fluorodichloromethyl)" should read
   -- (fluorodichloromethyl)- --.
Column 12, line 9, "(trichloromethyl)" should read
   -- (trichloromethyl)- --.
Column 12, line 25, "(fluorodichloromethyl)" should read
   -- (fluorodichloromethyl)- --.
Column 13, line 22, "trifluorometyl" should read
   -- trifluoromethyl --.
Column 14, line 4, after "...methyl" insert -- - --.
Column 14, line 32, before "benzene" insert -- - --.
```

Signed and Sealed this

Twelfth Day of December 1978

[SEAL]

Attest:

RUTH C. MASON
Attesting Officer

DONALD W. BANNER
Commissioner of Patents and Trademarks